(12) United States Patent
Noecker

(10) Patent No.: US 6,461,335 B1
(45) Date of Patent: Oct. 8, 2002

(54) TUBE DEPENDENT ANTI-FREE-FLOW VALVE

(75) Inventor: Angela M. Noecker, Richmond Heights, MO (US)

(73) Assignee: Sherwood Services, AG (CH)

( * ) Notice: Subject to any disclaimer, the term of this patent is extended or adjusted under 35 U.S.C. 154(b) by 0 days.

(21) Appl. No.: 09/514,667

(22) Filed: Feb. 28, 2000

(51) Int. Cl.$^7$ ............................................. A61M 5/00
(52) U.S. Cl. ........................ 604/246; 251/349; 251/354
(58) Field of Search ........................... 604/246, 167.06, 604/167.04, 170.01, 323, 174, 236, 249, 153; 137/893, 843, 845, 493, 67, 225, 522, 852

(56) References Cited

U.S. PATENT DOCUMENTS

| | | | |
|---|---|---|---|
| 3,311,268 | | 3/1967 | Fields .......................... 222/159 |
| 3,460,529 | | 8/1969 | Leucci ........................... 128/2 |
| 3,547,401 | | 12/1970 | Beall et al. .................. 251/144 |
| 4,337,770 | * | 7/1982 | Young et al. ................ 251/117 |
| 4,394,862 | * | 7/1983 | Shim ............................. 604/67 |
| 4,395,260 | | 7/1983 | Todd et al. .................. 604/122 |
| 4,527,588 | * | 7/1985 | Tseo et al. ................... 137/843 |
| 4,615,693 | | 10/1986 | Paradis et al. ............... 064/122 |
| 4,850,393 | | 7/1989 | Lashomb ..................... 137/528 |
| 4,263,932 | | 4/1991 | Laar et al. .............. 137/101.27 |
| 5,019,055 | | 5/1991 | O'Boyle ....................... 604/249 |
| 5,261,459 | * | 11/1993 | Atkinson et al. ............ 137/846 |
| 5,267,586 | | 12/1993 | Jankavaara .................. 137/565 |
| 5,396,925 | * | 3/1995 | Poli ............................. 137/493 |
| 5,853,397 | * | 12/1998 | Shemesh et al. ............. 604/247 |
| 5,868,715 | | 2/1999 | Tung ............................ 604/256 |
| 5,954,485 | * | 9/1999 | Johnston et al. | |
| 6,092,551 | * | 7/2000 | Bennett ........................ 137/846 |

FOREIGN PATENT DOCUMENTS

| | | | |
|---|---|---|---|
| CA | 2076512 | * | 8/1992 |
| CA | 50722/50 | * | 2/1994 |
| DE | 4126088 | * | 1/1993 |

* cited by examiner

Primary Examiner—Denise L. Esquivel
Assistant Examiner—Tu C. Nguyen
(74) Attorney, Agent, or Firm—Greensfelder, Hemker & Gale, P.C.

(57) ABSTRACT

The present invention relates to an anti-free-flow valve to prevent fluid free-flow through a tube assembly having a lumen. The valve device comprises a body disposed inside the lumen having a cylindrical portion formed adjacent a tapered portion, the cylindrical portion includes an opening and the tapered portion has a pair of beveled surfaces with ends that form a slit therebetween. The slit communicates with the opening through a passage formed through the body of the valve device. When the tube assembly is in a relaxed condition, the ends of the beveled surfaces confront one another and place the slit in the closed position which prevents fluid flow through the passage of the body and through the valve device. When a tensile force is applied along the tube assembly in an area adjacent the valve device, the inner diameter of the lumen decreases which elongates the body and urges the ends of the beveled surfaces away from one another and places the slit in the open position which permits fluid flow through the passage and out the body of the valve device.

28 Claims, 4 Drawing Sheets

TUBE DEPENDENT ANTI-FREE-FLOW VALVE

BACKGROUND OF THE INVENTION

1. Field of the Invention

The present invention relates to a device for preventing fluid free flow in a fluid administration system, and more particularly to an anti-free flow valve device disposed within a lumen of a tube assembly. More specifically, the present invention relates to a tube diameter dependent anti-free-flow valve device that prevents fluid free flow when the tube assembly is in a relaxed condition, while permitting uninhibited fluid flow when the tube assembly is in a stretched condition.

2. Prior Art

Administering fluid containing medicine or nutrition to a patient is generally well-known in the art. Typically, fluid is supplied to a patient by a tube assembly which provides a fluid pathway between a fluid source and a patient. The fluid is supplied to the patient through the tube assembly by either an enteral connection which accesses a visceral organ (gastrointestinal feeding) of a patient or through a parenteral connection which accesses a non-visceral organ (intravenous feeding).

Fluid flow rate through the tube assembly may be manually controlled by a mechanical clip which is designed to progressively occlude the tube assembly and selectively impede fluid flow induced by the force of gravity. One such mechanical clip which operates to occlude a portion of the tube assembly is a conventional roller clamp that has a hollow body with opposed outlets and a pair of angled slots formed opposite of one another transverse to the outlets. The clip further includes a wheel having an axle which is coupled to the body through the slots. A portion of the tube assembly is then inserted through both the outlets and the wheel axially advanced along the slots to pinch a portion of the tube against the body which progressively occludes the tube assembly. Although the mechanical clip operates to provide a cost-efficient method for controlling fluid flow rate, the clip must be manually actuated by the user. Further, the wheel of the mechanical clip can be inadvertently bumped or jostled out of position resulting in an inappropriate flow rate.

In order to better enhance fluid flow rate control in a fluid administration system, calibrated pumps have been utilized. One such calibrated pump is a peristaltic pump connected in-line along a portion of the tube assembly between the fluid source and the patient. The peristaltic pump advances the fluid through the tube assembly by progressively occluding successive portions of the tube assembly and urging each occluded portion forward. When a peristaltic pump is utilized to control the fluid flow rate, mechanical clips are typically not employed or are disengaged to prevent the clip from interfering with the operation of the pump.

Although peristaltic pumps have substantially advanced the art, further improvements are required. For example, once the tube assembly is disengaged from the pump fluid flow rate through the tube assembly becomes unrestrained as fluid is drawn through the tube assembly due to the force of gravity. This situation is known as fluid free flow and may present an undesirable, or even life-threatening situation, if left undetected because of the risk of overfeeding or overmedicating a patient.

In order to overcome the above-noted drawbacks to fluid administration systems utilizing pumps, several devices have been suggested which operate to automatically occlude a portion of the tube assembly and prevent fluid free flow when the tube assembly becomes disengaged from the pump while also permitting uninhibited fluid flow when the tube assembly is properly engaged to the pump. For instance, a variety of automatic occluders have been suggested to improve the art such as those disclosed in U.S. Pat. No. 4,689,043 to Bisha entitled "IV Tube Activator" which describes a clamp for use with a peristaltic pump. The clamp includes a V-shaped channel which is spring biased into a closed position where the narrow portion of the V-shaped channel is sized to substantially crimp, or occlude, a portion of the tube assembly and prevent fluid free flow therethrough. The clamp is placed in an open position by a handle which overlays the pump and depresses the springs such that the tube assembly is positioned within the wider portion of the V-shaped channel to permit unrestricted flow through the tube assembly when the pump is operating. When the handle is released, the V-shaped portion will automatically slide into the closed position and prevent fluid free flow by occluding a portion of the tube assembly.

Another automatic occluder is disclosed in U.S. Pat. No. 5,704,582 to Winterer, et al. entitled "Pinched Clipped Occluder for Infusion Sets" which describes a clip that is positioned between a housing and a cover of a pump. The clip has a plunger biased by a spring towards a portion of the tube assembly so that the lumen of the tube assembly becomes occluded by the plunger. Fluid flow through the tube assembly may only be established when the plunger is biased away from the lumen of the tube assembly which occurs when the cover is properly coupled with the housing. However, once the cover becomes disengaged from the housing, the plunger is automatically biased into the closed position by the spring to prevent fluid free flow.

Although both of the aforementioned automatic occluders have advanced the art, both devices are mechanically complex and prone to mechanical failure. In addition, the mechanical complexity of these devices also results in occluders which are expensive to manufacture. Accordingly, there is a need in the art for a simple valve device that is capable of preventing fluid free flow when the tube assembly is disengaged from the pump, while permitting uninhibited fluid free flow when the tube assembly is disengaged from the pump.

OBJECTS AND SUMMARY OF THE INVENTION

In brief summary, the present invention overcomes and substantially alleviates the deficiencies present in the art by providing a valve device for preventing fluid free-flow in a fluid administration system. The valve device of the present invention is disposed within the lumen of a tube assembly for preventing fluid free flow when the tube assembly is disengaged from the pump, while permitting uninhibited fluid flow when the tube assembly is engaged with the pump.

Preferably, the pump of the fluid administration system used in conjunction with the present invention includes a rotor for advancing fluid through the tube assembly and a pair of recesses positioned adjacent the rotor for retaining portions of the tube assembly to the housing of the pump during operation of the system. The tube assembly comprises three interconnected tube segments each having a distal and proximal ends for providing a fluid pathway between the fluid source and a patient. The fluid source is connected to the distal end of the first tube segment, while the proximal end thereof is connected to the distal end of the second tube segment by a drip chamber having an abutment surface. The proximal end of the second tube segment is interconnected to the distal end of the third tube segment by a coupling having an external flange. Finally, the proximal end of the third tube segment is attached to a patient through either an enteral or parenteral connection.

The tube assembly is engaged with the pump by threading a portion of the assembly around the rotor with the abutment surface of the drip chamber and external flange of the coupling engaged within the first and second recesses, respectively, of the pump. Preferably, the second tube segment as it is engaged around the rotor has a length which permits the abutment surface and the external flange to be properly captured by the first and second recesses and place the second tube segment in a stretched condition. Each of the tube segments has a lumen formed therethrough to allow the passage of fluid through the tube assembly. Alternatively, the valve device may be used with a tube assembly not having a drip chamber or coupling.

Preferably, the valve device of the present invention is disposed within the lumen of one of the tube segments to prevent fluid free-flow when the tube assembly is disengaged from the pump. The valve device comprises a body having a generally cylindrical portion formed adjacent a tapered portion. The cylindrical portion of the valve device includes an outlet and both the cylindrical portion and the outlet are generally circular in configuration. The tapered portion includes opposite beveled surfaces having ends with the beveled surfaces being bounded by a pair of side walls. Preferably, the beveled surfaces are planar in shape, while the side walls have a generally rounded configuration. The tapered portion also includes a slit formed between the ends of the beveled surfaces and a passage which interconnects the outlet and the slit of the valve device such that any fluid that enters through the slit can pass along the passage and exit from the outlet. Preferably, the valve device is disposed within the lumen of the second tube segment adjacent the coupling with the slit or proximal end of the valve device facing the proximal end of the second tube segment and the outlet directed towards the distal end thereof. The cylindrical portion of the valve device is sized and shaped to sealingly engage against the inner circumference of the lumen and prevent fluid flow around the valve device at all times.

When the second tube segment is in a relaxed condition or disengaged from the pump, the slit is placed in the closed position by the ends of the beveled surfaces confronting one another and occluding the lumen of the second tube segment. However, once a tensile force is applied along the second tube segment by stretching it, the second tube segment assumes a stretched condition which urges the ends of the beveled surfaces away from one another as the inner diameter of the lumen is decreased and elongates the body of the valve device. This action places the slit in the open position, thereby allowing fluid to pass through the lumen of the second tube segment. Once the applied tensile force is released by disengaging the tube assembly from the rotor, the inner diameter of the lumen increases and the body of the valve device returns to the relaxed condition. The expansion of the lumen when the tube assembly is in the relaxed condition permits the ends of the beveled surfaces to come together again and return the slit to the closed position. Alternatively, the slit may be placed in the open position by manually pinching the body of the valve device transverse to the slit which also causes the ends of the beveled surfaces to be urged away from one another as the inner diameter of the lumen is decreased.

In operation, the valve device of the present invention prevents fluid free flow whenever the tube assembly is disengaged from the pump while permitting uninhibited fluid flow when the tube assembly is engaged around the rotor of the pump, or the valve device is manually actuated by the user. The valve device is placed within the lumen of the tube assembly during manufacture. To utilize the valve device, the user first connects the first tube segment of the tube assembly with the fluid source and allows fluid to flow to the point where the valve device is located within the tube assembly. The user then primes the tube assembly in order to evacuate air from the remaining portions of the tube assembly and initiate fluid flow therethrough. Preferably, the tube assembly may be manually primed by stretching a portion of the tube assembly surrounding the valve device which urges the ends of the beveled surfaces away from one another as the body of the valve device elongates and opens the slit to fluid flow through the lumen of the tube assembly. Air is then forced out through the remaining portions of the tube assembly.

To regulate and urge the fluid through the tube assembly, the tube assembly is connected to the pump. Specifically, the abutment surface of drip chamber is engaged within the first recess of the pump and the second tube segment is stretched around the rotor. The external flange is then inserted into the second recess of the pump to retain the second tube segment in a stretched condition. Due to the tensile force applied to the second tube segment, the inner diameter of the lumen is decreased such that the lumen confronts and urges the pair of side walls together which urges the ends of the beveled surfaces away from one another to place the slit in the open position. Once in the open position, fluid flow is established through the lumen of the second tube segment. However, if the tube assembly becomes disengaged from the pump, the tensile force exerted upon the second tube segment will be released which automatically results in expansion of the inner diameter of the lumen so that the ends of the beveled surfaces confront one another and close the slit to fluid flow.

Accordingly, the primary object of the present invention is to provide a valve device which prevents fluid free-flow.

Another object of the present invention is to provide a valve device that prevents fluid free flow when the tube assembly is disengaged from the pump, while permitting uninhibited flow when the tube assembly is engaged to the pump.

Still another object of the present invention is to provide a valve device which may be automatically or manually actuated.

Yet another object of the present invention is to provide a valve device that is disposed within the lumen of the tube assembly.

A further object of the present invention is to provide a valve device which reduces manufacturing costs.

These and other objects of the present invention are realized in the preferred embodiment of the present invention, described by way of example and not by way of limitation, which provides for a valve device for use in a fluid administration system to prevent fluid free-flow.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
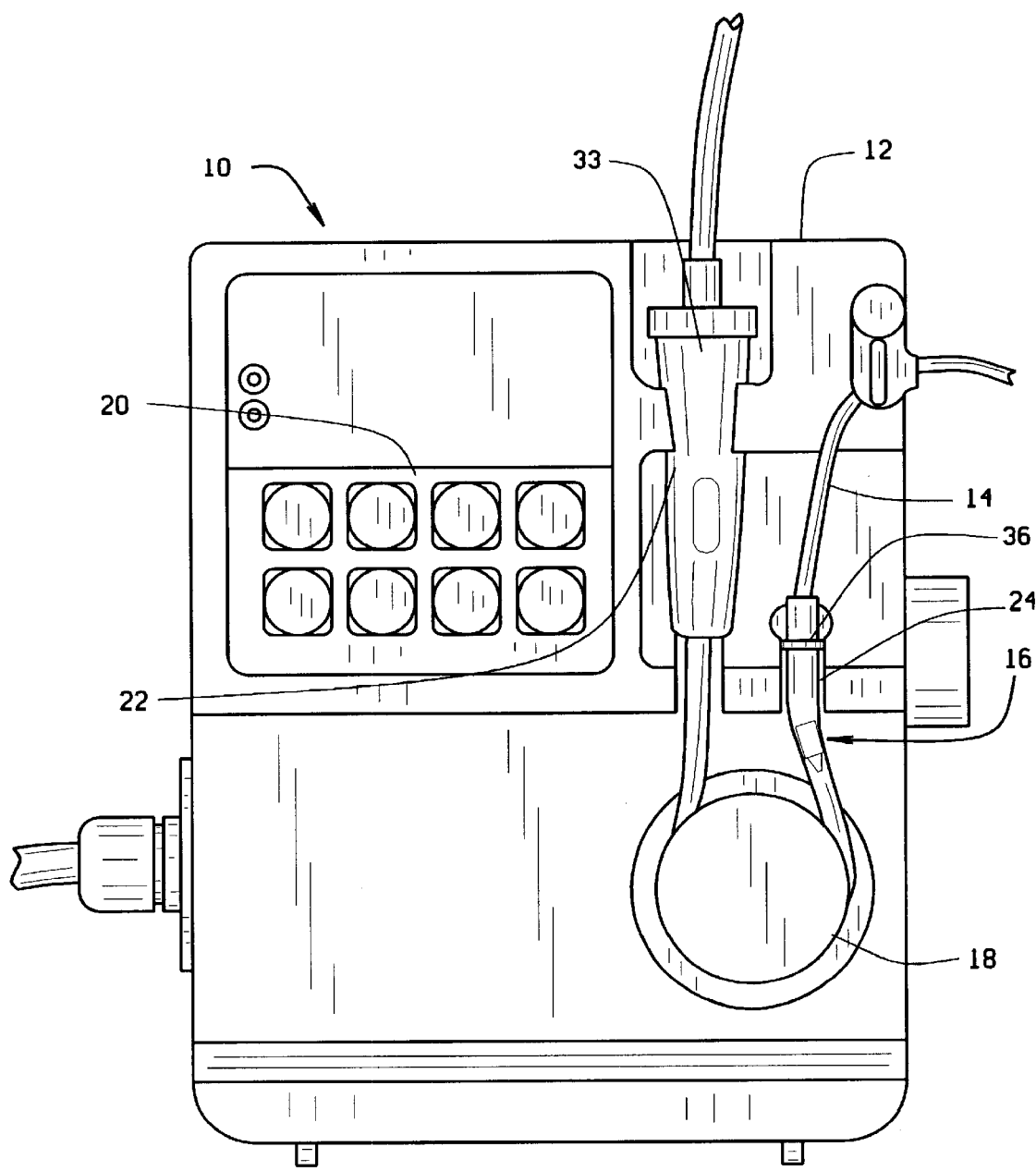
FIG. 1 is a partial fragmentary perspective view of a fluid administration system having a pump and a tubing assembly coupled thereto with a valve device disposed within the lumen of the tubing assembly according to the present invention.
Figure 2:
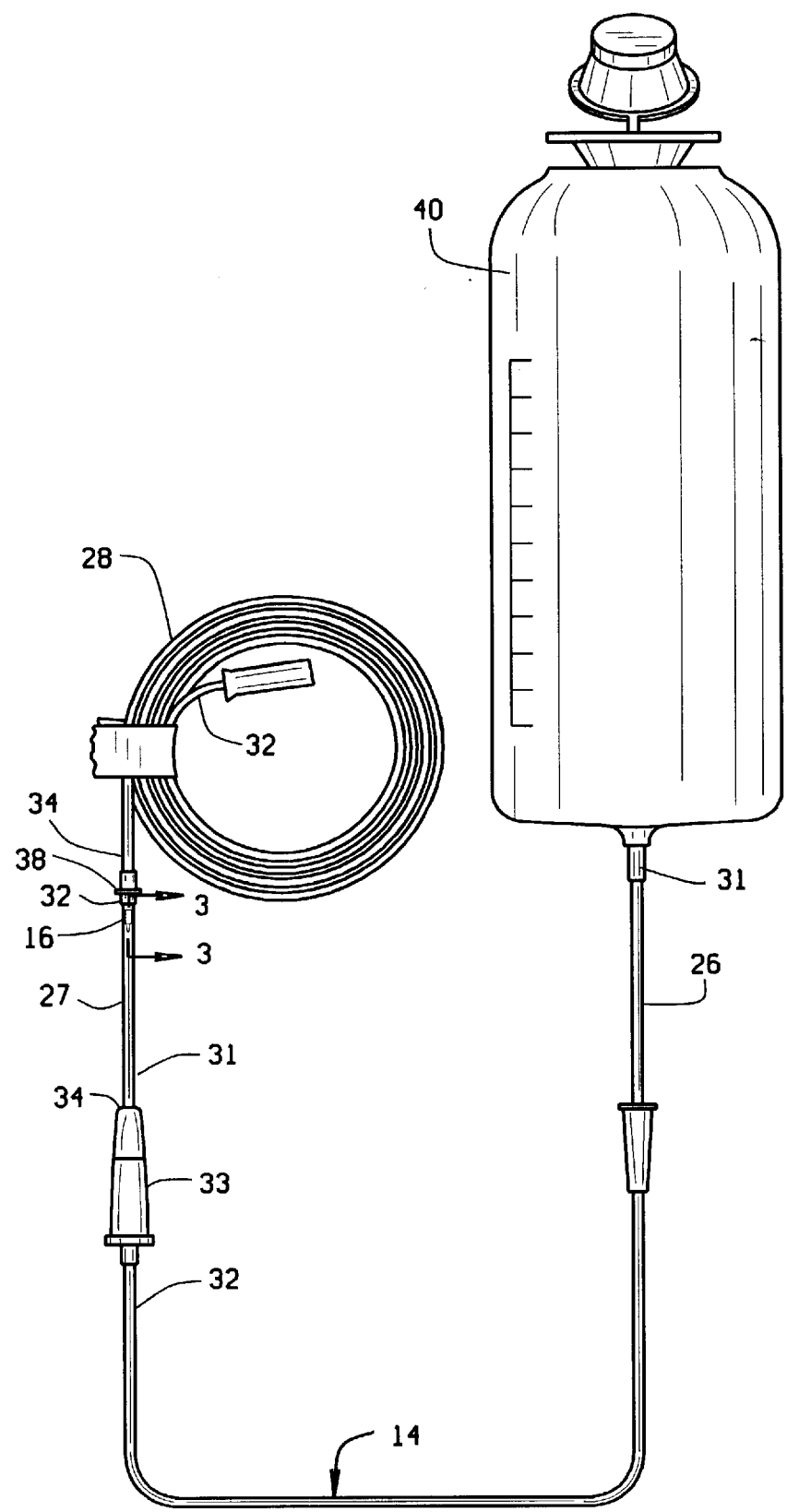
FIG. 2 is a front elevational view of the tube assembly and fluid source according to the present invention.

Referring to the drawings, the preferred embodiment of the valve device of the resent invention is illustrated and generally indicated as 16 in FIG. 1. The valve device 16 is used in a fluid administration system 10 which comprises a tube assembly 14 engaged with a pump 12 and a fluid source 40 (FIG. 2). For ease of reference, proximal shall refer to the end of the valve device 16 or tube assembly 14 farthest from fluid source 40, while distal shall refer to the end of device 16 or assembly 14 closest to fluid source 40.

Pump 12 is preferably a rotary peristaltic pump as shown in FIG. 1. Of course one skilled in the art can best appreciate that a variety of other pumps, such as a linear peristaltic pump, may be utilized without departing from the novel aspects of the present invention. Specifically, pump 12 includes a rotor 18 and a control panel 20 located adjacent rotor 18 which permits a user to monitor and adjust the rotation rate of rotor 18 for controlling fluid flow rate by pump 12. A first recess 22 and a second recess 24 are formed above rotor 18 for engaging portions of tube assembly 14 which will be discussed in greater detail below.

Referring to FIG. 2, tube assembly 14 includes a first tube segment 26, a second tube segment 27, and a third tube segment 28 which are in communication with one another. Each of the first, second and third tube segments 26, 27, and 28 have respective distal and proximal ends 31, 32. Connected to distal end 31 of first tube segment 26 is fluid source 40 for providing fluid to a patient while the proximal end 32 thereof is attached to a drip chamber 33. As further shown, drip chamber 33 has an abutment surface 34 which interconnects proximal end 32 of first tube segment 26 with distal end 31 of second tube segment 27. The proximal end 32 of second tube segment 27 is then interconnected to distal end 31 of third tube segment 28 by a coupling 36 having an external flange 38. Finally, third tube segment 28 terminates at a proximal end 32 which is attached to an enteral or parenteral connection (not shown) made with the patient for delivery of fluid.

Figure 6:
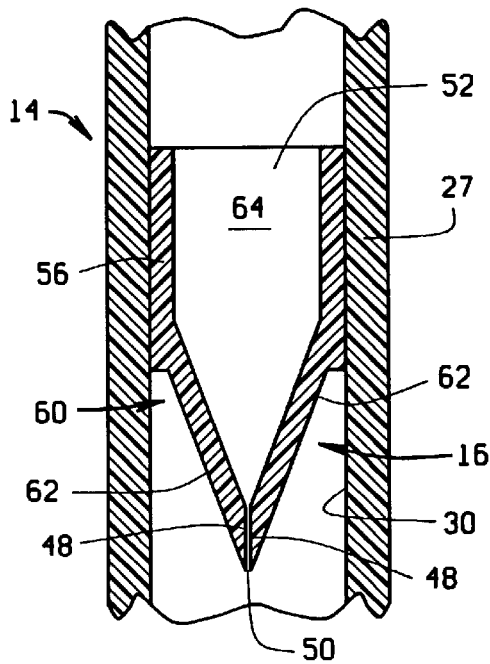
FIG. 6 is a cross-sectional view of the valve device taken along line 6—6 of FIG. 3 according to the present invention.

As illustrated in FIG. 1, drip chamber 33 and coupling 36 are sized and shaped to be captured within first recess 22 and second recess 24, respectively. Preferably, the length of second tube segment 22 permits drip chamber 33 and coupling 36 to be properly captured within first recess 22 and second recess 24, respectively, while also stretching second tube segment 27 as it is engaged around rotor 18. Accordingly, the amount of tensile force A (FIG. 9) applied along second tube segment 27 as it is engaged around rotor 18 may be varied by altering the length of tube segment 27. With reference to FIG. 6, each tube segment 26, 27 and 28 of tube assembly 14 includes a lumen 30 formed therethrough by which fluid may pass from fluid source 40.

Figure 3:
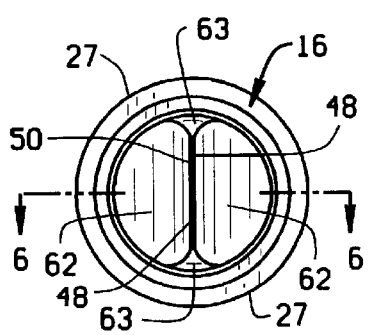
FIG. 3 is a front view of the valve device disposed within the lumen of the second tube segment with the slit in the closed position according to the present invention.
Figure 4:
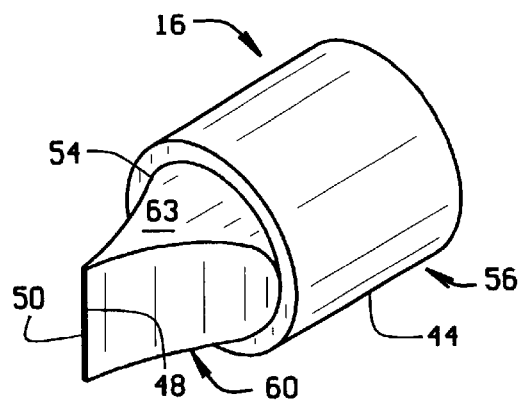
FIG. 4 is a perspective view of the valve device according to the present invention.
Figure 5:
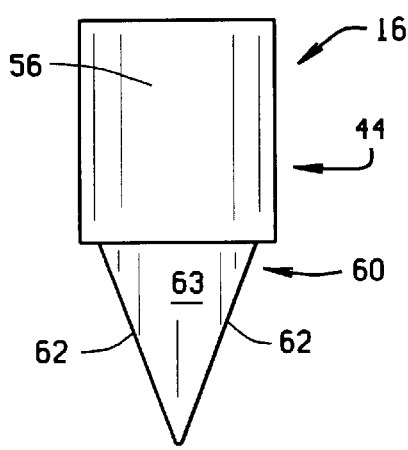
FIG. 5 is a side elevational view of the valve device according to the present invention.
Figure 7:
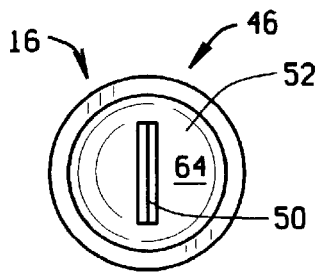
FIG. 7 is a rear elevational view of the valve device according to the present invention.

Referring to FIG. 4, valve device 16 comprises a hollow flexible body 44 having a tapered portion 60. With further reference to FIGS. 3 and 5, tapered portion 60 formed at a distal end 47 of body 44 includes opposing beveled surfaces 62 bounded by a pair of side walls 63 with surfaces 62 having ends 48 which define a slit 50. Body 44 further includes a proximal end 46, as shown in FIG. 7, which forms an outlet 52 in communication with a passage 64 such that fluid which enters slit 50 may pass along passage 64 and out outlet 52. As further shown in FIG. 4, the intersection between tapered portion 60 and cylindrical portion 56 defines a shoulder 54. However, in the alternative cylindrical portion 56 may simply taper gradually into tapered portion 60 without departing from the scope of the present invention.

Figure 8:
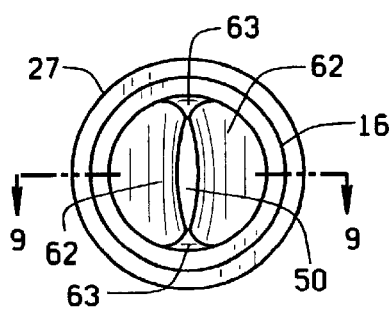
FIG. 8 is a front view of the valve device disposed within the lumen of the second tube segment with the slit in the open position. according to the present invention.
Figure 9:
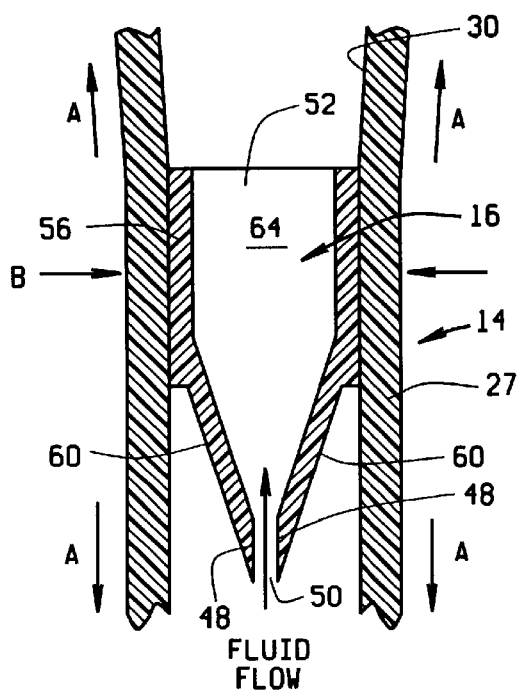
FIG. 9 is a cross-sectional view of the valve device taken along line 9—9 of FIG. 8 according to the present invention.

As shown in FIGS. 6 and 9, valve device 16 is preferably disposed within lumen 30 of second tube segment 27 adjacent coupling 36 (FIG. 2) with slit 50 facing the direction of fluid flow while outlet 52 is oriented toward proximal end 32 of third tube segment 28 (FIG. 2). The cylindrical portion 56 is sized and shaped to sealingly engage against the inner surface of lumen 30 and prevent fluid flow around valve device 16. When second tube segment is in a relaxed condition, the ends 48 of opposing beveled surfaces 62. substantially confront one another such that slit 50 is maintained in a closed position, thereby preventing fluid. flow through passage: 64 of hollow body 44. Referring to FIGS. 8 and 9, fluid flow may be established through valve device 16 by applying tensile force A along second tube segment 27 by engaging portion of tube segment 27 around rotor 18. When engaging second tube segment 27 around rotor 18, tube segment 27 is placed in a stretched condition as tensile force A is applied the talong. As further shown, tensile force A also causes a transverse force B to be applied to cylindrical portion 56 which decreases the inner diameter of the lumen 30 as a result of second tube segment 27 being placed in the stretched condition. In the stretched condition body 44 becomes elongated which urges the ends 48 of opposing beveled surfaces 62 away from one. another and opens slit 50 to permit fluid flow therethrough. Referring to FIG. 6, once second tube segment 27 is disengaged from rotor 18, tensile force A and transverse force B cease and tube segment 27 is returned to the relaxed condition. In the relaxed condition, ends 48 of opposing beveled surfaces 62 confront one another, thereby placing slit 50 in the closed position and prevent fluid free flow.

Figure 10:
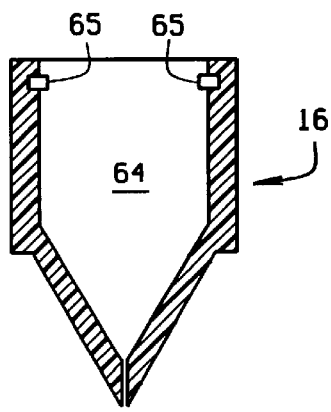
FIG. 10 is a partial cross-sectional view of the valve device showing slots adapted to retain an insert according to the present invention.
Figure 11:
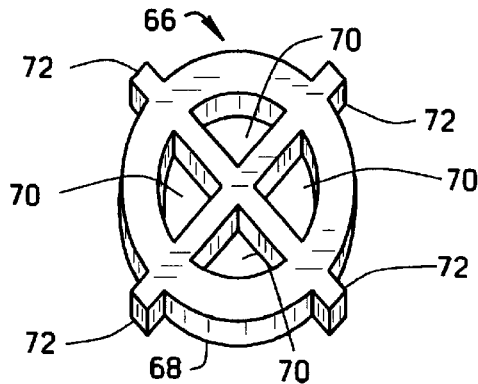
FIG. 11 is a perspective view of the preferred embodiment of an insert having a thin oval body according to the present invention.

One skilled in the art can appreciate that the decrease in the inner diameter of lumen 30 is directly proportional to the tensile force applied to second tube segment 27. Accordingly, the amount second tube segment 27 is stretched due to the tensile force applied thereto may be modified by changing the length of second tube segment 27. Alternatively, the amount that the inner diameter of lumen 30 is decreased may be accomplished by pre-stressing body 44 of valve device 16 in a direction approximately transverse to slit 50, thereby biasing body 44 into a generally oval shaped configuration. Preferably, valve device 16 may be pre-stressed by placing an oval-shaped insert 66, as shown in FIG. 11, into passage 64 of body 44. The preferred embodiment of insert 66 comprises a thin oval body 68 defining apertures 70 for allowing fluid flow therethrough. In addition, insert 66 also includes tabs 72 which are sized and shaped to be received within a respective slots 65 formed along the inner surface of passage 64, as illustrated in FIG. 10, for facilitating retention of insert 66 within valve device 16. It is contemplated that insert 66 may have one or more tabs 72 or one or more apertures 70.

Figure 12:
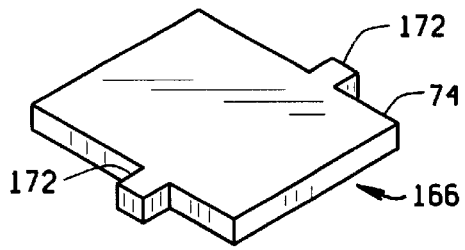
FIG. 12 is a perspective view of an alternative embodiment of the insert having an elongated rectangular body according to the present invention.
Figure 13:
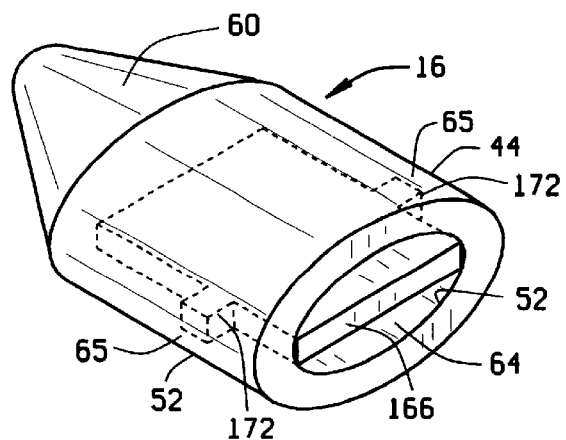
FIG. 13 is a perspective view of the valve device with the alternative embodiment of the insert of FIG. 12 shown in partial phantom.

One skilled in the art can appreciate that a variety of other methods may be utilized to pre-stress valve device 16 into an oval shaped configuration such that the major diameter of insert 66 is transverse to the slit 50. For example, the present invention also contemplates a variety of alternative embodiments of insert 66. As illustrated in FIGS. 12 and 13, one alternative embodiment is insert 166 which is shown having a generally rectangular-shaped body 74 which biases body 44 into a generally oval shaped configuration when inserted through opening 52 and retained within passage 64 by opposing tabs 172 which securely engage slots 65 formed along the inner surface of passage 64.

Figure 14:
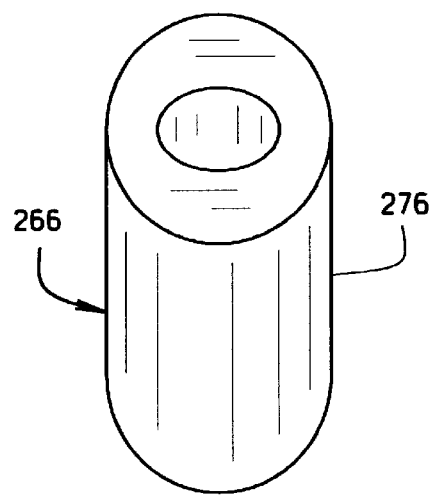
FIG. 14 is a perspective view of another alternative embodiment of the insert having an elongated oval body according to the present invention.

In another alternative embodiment shown in FIG. 14, insert 266 has an elongated oval body 276 with no tabs required to retain insert 266 inside valve device 16. Insert 266 is inserted through opening 52 and substantially fills passage 64 such that body 44 takes a generally oval shaped configuration.

In operation, the user of the present invention connects the distal end 31 of first tube segment 26 with fluid source 40 and permits fluid flow through lumen 30 until the fluid reaches the point where valve device 16 is disposed within tube assembly 14. With tube assembly 14 in a relaxed condition and disengaged from pump 12, valve device 16 prevents fluid free flow into third tube segment 28. Preferably, air is cleared from third tube segment 28 when the user primes tube assembly 14 by applying a tensile force A along the area of the tube assembly 114 adjacent valve device 16 to place second tube segment 27 in the stretched condition and open slit 50 to fluid flow. Applying tensile force A causes second tube segment 27 to stretch which in turn exerts a transverse force B against body 44 that decreases the inner diameter of lumen 30. The decrease in the inner diameter of lumen 30 elongates body 44 and urges the ends 48 of opposing beveled surfaces 62 away from one another, thereby placing slit 50 in the open position and allow fluid flow therethrough. Alternatively, the user can manually prime the tube assembly 14 by pinching body 44 of valve device 16 in a direction transverse to slit 50. By pinching valve device 16 in this manner, the ends 48 of the opposed beveled surfaces 62 are urged away form one another which opens slit 50 such that fluid flow may be established through lumen 30. Once all the air is cleared from tube assembly 14, the proximal end 32 of third tube segment 28 may be connected to an enteral or parenteral connection on the patient.

To regulate and urge the fluid through tube assembly 14, a pump 12 is connected in-line along tube assembly 14. Specifically, abutment surface 34 of drip chamber 33 is engaged with first recess 22 and second tube segment 27 is stretched by the user around rotor 18. The external flange 38 of coupling 36 is then engaged within second recess 24 in order to retain second tube segment 27 in the stretched condition. Due to the tensile force applied along second tube segment 27, the inner diameter of lumen 30 is decreased such that the inner surface of lumen 30 confronts and elongates body 44. When body 44 becomes elongated, the ends 48 of opposed beveled surfaces 62 are urged away from one another and slit 50 is placed in the open position, thereby permitting fluid flow through passage 64 and out outlet 52. However, if tube assembly 14 becomes disengaged from pump 12, the tensile force exerted along second tube segment 27 will be released which automatically results in expansion of the inner diameter of opposed lumen 30 so that the ends 48 of opposing beveled surfaces 62 confront one another and place slit 50 in the closed position which prevents fluid flow through body 44.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

I claim:

1. A valve for use with a fluid administration system for preventing fluid free flow through a tube assembly having a lumen, the tube assembly being connected between a patient and a fluid source, said valve comprising:

a body disposed inside the lumen of the tube assembly, the body including a cylindrical portion having an opening at one end and a tapered portion formed adjacent the other end of said body, said tapered portion having beveled surfaces opposite of one another with ends that define a slit between said ends, a passage formed between said opening and said slit, said lumen having an inner diameter that decreases upon stretching of the tube assembly, wherein when the tube assembly is in a relaxed condition said ends of said beveled surfaces confront one another and prevent fluid free flow through said slit and when the tube assembly is in a stretched condition said ends of said beveled surfaces are urged away from one another by the decrease in the inner diameter of the lumen and permit fluid flow through said slit.

2. The valve according to claim 1, wherein said body is made of a flexible material.

3. The valve according to claim 1, wherein said body elongates when the tube assembly is in said stretched condition.

4. The valve according to claim 1, wherein said body is made from a flexible material.

5. The valve according to claim 1, wherein said is made valve further comprises an insert inserted within said passage.

6. The valve according to claim 5, wherein said insert comprises:

an insert body having at least one aperture formed therethrough and at least one tab extending from said insert body.

7. The valve according to claim 6, wherein said valve further comprises at least one slot formed along said passage which is sized and shaped to receive said tab for retaining said insert inside said passage.

8. The valve according to claim 6, wherein said insert body has a generally thin oval shape.

9. The valve according to claim 6, wherein said insert body has a generally elongated square shape.

10. The valve according to claim 6, wherein said insert body has a generally elongated oval shape.

11. A tube assembly for use with a fluid administration system connected between a patient and a fluid source by a tube assembly, said tube assembly comprising:

at least one tube segment having a lumen therethrough; and a valve disposed within said lumen and sealing said lumen to fluid flow therethrough, said valve having a body including a cylindrical portion having an opening and a tapered portion formed adjacent said cylindrical portion, said tapered portion having a slit, and a passage formed between said opening and said slit, said lumen having an inner diameter that decreases upon stretching of the tube assembly, wherein when said at least one tube segment is in a relaxed condition said slit is placed in a closed position which prevents fluid free flow through said passage and when said at least one tube segment is in a stretched condition said slit is placed in an open position by the decrease in the inner diameter of the lumen which permits fluid flow through said passage.

12. The tube assembly according to claim 11, wherein said at least one tube segment comprises:

a first tube segment;

a second tube segment connected to said first tube segment; and a third tube segment connected to said second tube segment.

13. The tube assembly according to claim 12, wherein said tube assembly further comprising:

a drip chamber interconnected between said first tube segment and said second tube segment; and a coupling interconnected between said second tube segment and said third tube segment.

14. The tube assembly according to claim 11, wherein the valve is formed from an elastically deformable material.

15. The tube assembly according to claim 11, wherein said body elongates when said at least one tube segment is in said stretched condition.

16. The tube assembly according to claim 11, wherein said an inner diameter of said lumen decreases when said at least one tube segment is in said stretched condition.

17. The tube assembly according to claim 11, wherein said tapered portion further comprises opposing beveled surfaces with ends which form said slit.

18. The tube assembly according to claim 11, wherein said valve further comprises an insert fitted within said passage.

19. The tube assembly according to claim 18, wherein said insert comprises:

an insert body having at least one opening formed therethrough and at least one tab extending from said insert body.

20. The tube assembly according to claim 19, wherein said insert body has a generally thin oval shape.

21. The tube assembly according to claim 19, wherein said insert body has a generally elongated square shape.

22. The tube assembly according to claim 19, wherein said insert body has a generally elongated oval shape.

23. The tube assembly according to claim 19, wherein said body has a generally elongated oval shape.

24. A method for preventing fluid free-flow in a fluid administration system which is interconnected between a fluid source and a patient, the method comprising the steps of:

(a) providing a fluid administration, including a pump and a tube assembly having two ends and a lumen formed therethrough, the fluid administration system further including a valve disposed within the lumen, the valve comprising a body, the body including a cylindrical portion with an opening formed at one end and a tapered portion formed adjacent another end of the cylindrical portion, the tapered portion including opposing beveled surfaces with ends that define a slit between the ends;

(b) attaching one end of said tube assembly to a fluid source;

(c) attaching said tube assembly to the pump such that said tube assembly stretches and elongates the body of the valve;

(d) decreasing the inner lumen of the tube assembly when said tube assembly is stretched; and (e) attaching the other end of the tube assembly to a patient.

25. The method according to claim 24, wherein when the body elongates said slit is placed in an open position which permits fluid flow through said passage of the body.

26. The method according to claim 24, wherein when one end of the tube assembly is attached to the fluid source, the slit is placed in a closed position which prevents fluid free flow through the passage of the body.

27. The method according to claim 25 wherein when the slit is in the closed position, the ends of the opposing beveled surfaces confront one another and prevent fluid flow through the passage of the body.

28. The method according to claim 24, wherein attaching the tube assembly to the pump causes fluid to flow through the body of the valve.

* * * * *